United States Patent
Eggert et al.

(10) Patent No.: US 9,707,345 B2
(45) Date of Patent: Jul. 18, 2017

(54) METHOD AND MEDICAL DEVICE FOR ADJUSTING DOSE OF FLUID MEDICAMENT

(71) Applicant: SANOFI-AVENTIS DEUTSCHLAND GMBH, Frankfurt am Main (DE)

(72) Inventors: Ilona Eggert, Frankfurt am Main (DE); Michael Caspers, Frankfurt am Main (DE); Daniel Thomas De Sausmarez Lintell, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/359,858

(22) PCT Filed: Nov. 21, 2012

(86) PCT No.: PCT/EP2012/073253
§ 371 (c)(1),
(2) Date: May 21, 2014

(87) PCT Pub. No.: WO2013/076151
PCT Pub. Date: May 30, 2013

(65) Prior Publication Data
US 2015/0025493 A1   Jan. 22, 2015

(30) Foreign Application Priority Data
Nov. 23, 2011   (EP) ..................... 11190342

(51) Int. Cl.
*A61M 5/24* (2006.01)
*A61M 5/315* (2006.01)
(Continued)

(52) U.S. Cl.
CPC .......... *A61M 5/2448* (2013.01); *A61M 5/142* (2013.01); *A61M 5/2066* (2013.01);
(Continued)

(58) Field of Classification Search
CPC .... A61M 5/19; A61M 5/2066; A61M 5/2448; A61M 5/31596; A61M 5/31533;
(Continued)

(56) References Cited

U.S. PATENT DOCUMENTS 4,360,323 A * 11/1982 Anderson ........... A61M 1/1656
                                                                     137/99
5,240,146 A    8/1993  Smedley et al.
(Continued)

FOREIGN PATENT DOCUMENTS

EP      2283885 A1    2/2001
JP     62502876 A    11/1987
(Continued)

OTHER PUBLICATIONS

Meece, Jerry. "Pharmacoeconomic Advantages of Insulin Analogs." USPharmacist. Jobson, Dec. 22, 2006. Web. Aug. 4, 2015.*
(Continued)

*Primary Examiner* — Imani Hayman
*Assistant Examiner* — James D Ponton
(74) *Attorney, Agent, or Firm* — McDonnell Boehnen Hulbert & Berghoff LLP

(57) ABSTRACT

The invention relates to a method for delivering at least one fluid medicament from a medical device. The invention also relates to a medical device. The technical problem of improving the dose accuracy is solved by a method for delivering at least one fluid medicament from a medical device comprising a first reservoir containing a first fluid medicament, a second reservoir containing a fluid, and a fluid element connected to said first reservoir and said second reservoir. The method comprises receiving information about a desired dose of the first fluid medicament to be ejected, adjusting said dose to be ejected from said first reservoir based at least in part on information about a (Continued)

content of said fluid element, and ejecting said adjusted dose from said first reservoir through said fluid element. The technical problem is further solved by a medical device configured to work according to the method.

14 Claims, 13 Drawing Sheets

(51) Int. Cl.
    *A61M 5/20*     (2006.01)
    *A61M 5/142*     (2006.01)
    *A61M 5/14*     (2006.01)

(52) U.S. Cl.
    CPC .... *A61M 5/31535* (2013.01); *A61M 5/31545* (2013.01); *A61M 2005/1402* (2013.01); *A61M 2005/14208* (2013.01)

(58) Field of Classification Search
    CPC ............ A61M 5/31545; A61M 5/3155; A61M 5/31565; A61M 5/31573; A61M 5/3159; A61M 2005/1402; A61M 2005/14208; A61M 5/172; A61M 5/31535; A61M 5/31536; A61M 5/31546–5/31563
    See application file for complete search history.

(56) References Cited

U.S. PATENT DOCUMENTS

| | | | |
|---|---|---|---|
| 5,876,380 A | | 3/1999 | Manganini et al. |
| 6,302,855 B1 | * | 10/2001 | Lav et al. ...................... 600/584 |
| 2009/0216100 A1 | * | 8/2009 | Ebner .................. A61B 5/0002 |
| | | | 600/347 |
| 2009/0299328 A1 | * | 12/2009 | Mudd et al. .................. 604/506 |
| 2010/0087785 A1 | * | 4/2010 | Tschirren et al. ............. 604/208 |
| 2010/0137830 A1 | * | 6/2010 | Glejbol .................. A61M 5/148 |
| | | | 604/506 |

FOREIGN PATENT DOCUMENTS

| | | |
|---|---|---|
| JP | 6503292 | 4/1994 |
| JP | 2005510305 A | 4/2005 |
| JP | 2010519993 A | 6/2010 |
| WO | 8606861 A1 | 11/1986 |
| WO | 8606967 A1 | 12/1986 |
| WO | 9100748 A1 | 1/1991 |
| WO | 9210425 A1 | 6/1992 |
| WO | 03045474 A1 | 6/2003 |
| WO | 2008107378 A1 | 9/2008 |

OTHER PUBLICATIONS

English Translation of First Office Action issued i Chinese Patent Application No. 201280067452.0 dated Oct. 9, 2015.

* cited by examiner

METHOD AND MEDICAL DEVICE FOR ADJUSTING DOSE OF FLUID MEDICAMENT

CROSS REFERENCE TO RELATED APPLICATIONS

The present application is a U.S. National Phase application pursuant to 35 U.S.C. §371 of International Application No. PCT/EP2012/073253 filed Nov. 21, 2012, which claims priority to European Patent Application No. 11190342.3 filed Nov. 23, 2011. The entire disclosure contents of these applications are herewith incorporated by reference into the present application.

FIELD OF INVENTION

The invention relates to a method for delivering at least one fluid medicament from a medical device. The invention also relates to a medical device. In particular, the invention relates to a method and a medical device for delivering at least two drug agents from separate reservoirs. Such drug agents may comprise a first and a second medicament. The medical device includes a dose setting mechanism for delivering the drug agents automatically or manually by the user.

BACKGROUND

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.
2. Attach a dose dispenser, such as a double-ended needle assembly, to a distal end of the dispense interface. In this manner, a proximal end of the needle assembly is in fluidic communication with both the primary compound and secondary compound.
3. Dial up/set a desired dose of the primary compound from the injection device, for example, via a graphical user interface (GUI).
4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.
5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.
6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

As mentioned above, the different reservoirs, in particular a first and a second reservoir, are normally connected by fluid elements, such as fluidic channels, valves and fluidic chambers, in order to combine the flow path of the two medicaments and to eventually dispense the different medicaments or drug agents via a common outlet. This is especially desirable, because in case the medicaments are injected via a needle under the skin of the user, only a single needle is needed to be able to inject more than one medicament or drug agent.

On the one hand, it is practically unavoidable to leave a certain amount of the dispensed medicaments or fluids in the fluid elements attached to the reservoirs which may result in a waste of medicament. On the other hand, leaving the fluid elements filled with fluid may be desired since it should be avoided to dispense air into the skin of the user, for example. However, the remaining medicaments in the fluid elements negatively affect the accuracy of a desired dosage of the medicaments, unless the user primes a volume that is big enough to full flush the system and fluidically set it in a defined state. Of course, it is possible to reduce the volume of the fluid elements between the reservoirs and the actual injection site, though there are limits dictated by design, for example.

It may also be possible to flush or rinse the fluid elements with one or the other medicament, though this results in an undesired wastage of medicaments.

In view of the aforementioned the invention faces the technical problem of improving the dose accuracy.

The technical problem is solved by a method for delivering at least one fluid medicament from a medical device comprising a first reservoir containing a first fluid medicament, a second reservoir containing a fluid, and a fluid element connected to said first reservoir and said second reservoir. The method comprises receiving information about a desired dose of said first fluid medicament to be ejected, adjusting said dose to be ejected from said first reservoir based at least in part on information about a content of the fluid element, and ejecting the adjusted dose from the first reservoir through the fluid element. In addition, a supplementary dose of said fluid from said second reservoir can be ejected, for example after ejection of the dose of the first fluid medicament. The supplementary dose of said fluid may be a fixed dose, or the supplementary dose of said fluid may be adjusted as well. The adjustment of said supplementary dose of said fluid may be based at least in part on the same information as the adjustment of the dose of the first medicament, that is on the information about the content of the fluid element. The adjustment of the doses can be done before or during the ejection process.

By adjusting the dose to be ejected based upon the information about the content of the fluid element, the remaining fluid medicaments in the fluid element can be considered during a delivery process, yielding a higher resultant dose accuracy. Moreover no rinsing or flushing of the fluid elements is necessary saving medicaments and power of the medical device performing the method. The latter is especially advantageous for portable devices with a limited amount of power or for particularly expensive drug formulations.

The dose which the user or the device wants to deliver is either set by the user manually or it can be provided or calculated by the device, for example. The information about the desired dose may be a specific instruction, such as a number of specific units relevant to measure the amount of the drug to be administered. If there is no adjustment, even though the right amount of medicaments are ejected from the one or more reservoirs, the actual dosage eventually delivered to the user will be different from what was ejected due to the influence of the content of the fluid element, into which and through which the dose is ejected. With the adjustment this effect is compensated for.

The adjustment is preferably performed by a logic unit such as a control unit, a microprocessor or the like running software, for example. The desired dose to be delivered can be inputted by the user and may then be received by the responsible units, such as the control unit. Before a matching amount of the medicaments of the first and/or the second reservoir are then ejected, the information about the content of the fluid element is taken into account and, if necessary, a corrected amount or an adjusted dose is ejected from the first and/or second reservoir.

The ejection may be performed via mechanical means, such as springs or by an electromechanical device transforming the adjusted dose into a corresponding mechanical movement of a bung, for example.

The information about the content of a fluid element is understood to mean for instance the composition of the content or the distribution or homogeneity of the single components within the fluid element or further properties of the fluids. This content may be measured with sensors for example, though preferably it is calculated or estimated based on certain variables or the history of the device, such as one or more previous dosages.

The term fluid element is understood to mean any kind of typical element of a fluidic system. Such fluid elements may comprise fluidic channels, conduits, tubes, valves or a valve system or different types of fluidic chambers forming before or after valves, for example.

The fluid in the second reservoir may be used to dilute the first fluid medicament. However, the fluid in the second reservoir may also contain a second medicament. The first and the second medicament are preferably different. That means that they may differ in their active agents, or they may also comprise the same active agent in a different concentration for example.

When a first and a second medicament is administered, in particular one after another, it may be especially advantageous, if the dose of one of the medicaments is decreased, while the dose of the other medicament is increased, in order to adjust the dose to be ejected.

The information about said content of said fluid element may be based at least in part on a previous ejection from the first reservoir and/or the second reservoir.

If previous ejections or information about one or more previous ejections are used, a good approximation of the content of the fluid element or elements can be provided with little effort. This approximation can for example be provided by a calculation or by stored data in form of a look-up table, directly relating the relevant information about the content of the fluid element with the previous ejections. The previous ejections from the first reservoir and/or the second reservoir are in particular due to previous drug deliveries to the user.

Especially the directly preceding ejection has a big impact on the content of the fluid element. Thus a consideration of only the directly preceding ejection may be sufficient in many cases. Complicated calculations can thus be avoided.

For this purpose, information about previous deliveries or ejections can be saved in a memory unit, for example. Though, it is also possible to save the relevant information about the determined content of the fluid element instead of or together with information about the previous delivery.

To determine information about the content of the fluid element, it is possible to not only rely upon the information about at least one previous ejection from the first reservoir and/or the second reservoir. The information about said content of said fluid element can also be based at least in part on further variables or indicators, such as temperature of the medical device, a movement of the medical device, properties (e.g. viscosity) of the fluid or the first fluid medicament, or a time between single deliveries. Thus, the information about the content of the fluid element can be determined more precisely.

The information about said content of said fluid element can also be based at least in part on the last priming and subsequent ejections.

Priming is generally understood as ejecting only a small amount—for example only a tenth of an average dose—of a medicament from the first and/or the second reservoir, such that a small amount of liquid is ejected thorough the fluid element out of the medical device. This way the user can make sure that the medical device is working and that the fluid element is not blocked, for example. Additionally it can be made sure, that the fluid element is completely filled with a medicament and not with air, for example. Thus, many users use this priming from time to time or even before every administration.

The effect of priming the medical device can be taken advantage of in order to adjust the dose to be ejected from the first reservoir and/or from the second reservoir, since it can be approximated, that after a priming process the content of the fluid element is at least approximately reset to a known state, information about which can be saved in the medical device, for example. Thus the history of the device previous to the priming, for example after preceding ejections, the temperature or movement of the device, can be neglected without compromising the dose accuracy of the next delivery. If a priming operation is performed directly before a delivery, no further previous ejections need to be taken into account.

There may also be different modes of priming depending on whether the medical device is primed for the first time, for example after a dispense interface comprising the fluid element is exchanged or after cartridges comprising the reservoirs are exchanged, or whether the device is primed multiple times because of a user instruction. These different modes of priming can be accounted for during the delivery of the dose.

Further, information about said content of said fluid element is based at least in part on the time elapsed since the last ejection, since diffusion processes are time dependent and the amount of diffusion may take influence on the content of the fluid element.

By taking the time which has elapsed since the last ejection into account, a further improvement of the dose accuracy can be achieved. The first and the second medicament, which are guided through the fluid element, do not necessarily distribute evenly or homogeneously in the fluid element due to inherent flow turbulence effects, which are themselves determined for example by the flow velocity and channel geometry, providing an inhomogeneous content of the fluid element. This is especially the case, when the first and second medicaments are ejected one after another from the reservoirs. In this case the medicament ejected last will partly push out the medicament ejected first. The remaining amount of the medicament ejected first is concentrated in corners and at the border areas, for example. Thus, if a dose delivery takes place only short time after, there will only be a slightly higher dose of the medicament ejected first in the subsequent delivered dose, which needs to be adjusted. However, if there is a significant amount of time until a subsequent dose delivery the medicament ejected first and the medicament ejected second start to mix due to diffusion processes or movement of the medical device. Thus there is a more homogeneous distribution in the fluid element. Consequently, compared to the scenario where less time has elapsed, there will be a higher dose of the medicament ejected first in a subsequent dose delivery, which needs to be adjusted.

For this purpose, the medical device may comprise a timer to measure relevant time intervals. It is also possible to not only take into account the time which has elapsed since the last ejection in order to determine information about the content of the fluid element, but also to combine this embodiment with other embodiments of the method according to the invention.

According to another embodiment, the information about said content of said fluid element is based at least in part on a temperature of the medical device. In this manner, a further improvement of the dose accuracy is achieved. The temperature influences the rate at which diffusion takes place, for example. Thus the distribution of the components of the content in the fluid element is altered as a function of temperature among others. The medical device can comprise a temperature sensor in order to measure the temperature, for example in the device or in the fluid medicaments. The temperature profile may be recorded and/or saved continuously. However, it is also possible to determine an average temperature, for example. It is further possible to combine this embodiment with other embodiments to further improve the accuracy of dosing.

When the movement of the medical device is taken into account to determine the content of the fluid element, the accuracy of the doses can be further increased. Similar to an increased temperature, an extensive movement of the device chiefly promotes the mixing of the content of the fluid element. Therefore, the adjustment of the dose to be ejected is dependent upon such a movement. For this purpose, the medical device can comprise a motion detection unit, such as an accelerometer sensor, for example. Thus, shaking and agitation can be taken into account for the adjustment of the dose to be ejected. It is also possible to provide an agitation member, such as a ball, inside the fluid member in order to promote mixing of the content of the fluid element. Thus an accelerated mixing can be artificially provided, eliminating possible variations in the mixing processes due to environmental influences such as the temperature. This provides a further improvement of the dose accuracy, since the information about the content of the fluid element is improved and so is the adjustment of the dose to be ejected.

It is further possible to combine this embodiment of the method according to the invention with other embodiments to further improve the accuracy of dosing.

According to another embodiment, information about said content of said fluid element is based at least in part on one or more properties of the fluid and/or the fluid medicament. A further improvement of the dose accuracy can be achieved in this way, since the content of the fluidic element can be determined more precisely. Such properties are for example the viscosity or specific diffusion properties of the fluid medicaments. It is possible to combine this embodiment of the method according to the invention with other embodiments to further improve the accuracy of dosing.

According to another embodiment of the method according to the invention, the content of the fluidic element is determined based at least in part on a look-up table. By providing a look-up table, complex computations do not need to be done by the medical device itself and the same or similar computations do not need to be made repeatedly. Especially the solving of differential equations needed to calculate diffusion processes consume a lot of time and power. The look-up table provides information about the specific content of the fluid element for instance to a control unit, which can subsequently adjust the dose to be ejected from the first and/or the second reservoir, such that the desired dose is delivered. The look-up table may also provide information on how to adjust the dose ejected from the first and/or the second reservoir. The data of the look-up table can be based on empirical values or they may be calculated beforehand. Especially for portable medical devices and in case complex calculations need to be avoided a look-up table provides a possibility to increase accuracy without increasing the use of resources, such as battery life, for example.

If the information about the content of the fluid element is determined by calculation on the other hand, a more precise adjustment for the dose to be ejected from the first and/or the second reservoir can be achieved. The calculation can in particular be based on a formula either derived from experimental data or theoretical models. The calculation can in particular depend on previous ejections, temperature data, properties of the fluid medicaments and/or other data of the device history such as the amount of agitation or the like.

A further improvement of the dose accuracy can be achieved, when the medicament of the first reservoir and the fluid of the second reservoir are ejected one after another. In case more than one medicament needs to be ejected to achieve the desired dose, an ejection one after another results in less complex fluid dynamics compared to a simultaneous ejection of the first and the second medicament. Thus a more reliable prediction of the actual content of the fluid element can be achieved. Eventually, this further improves the dose accuracy of the desired dose. Additionally, power can be saved when the medicaments are not ejected simultaneously, since less powerful electromechanical devices, such as a stepper motor or a brushless dc motor, can be used, which allows for a lower average power consumption.

It is further preferred, when the first reservoir contains a first medicament and when the second reservoir contains a mixture of the first medicament and a second medicament. In case the second medicament needs to be delivered in a much lower dosage than the first medicament, for example, a higher dose accuracy can be achieved when in the second reservoir the second medicament is solved in the first medicament. Thus a larger volume from the second reservoir is ejected for the same amount of the second medicament, which can be more precisely adjusted than smaller volumes. Additionally, an uneven usage of the different reservoirs can be avoided, so that a medicament, which is needed less frequently or in lower dosages does not remain unused, for example.

In particular the second medicament comprises at least one active drug agent comprised by the first medicament.

It is also possible to provide more than two reservoirs, which can comprise a medicament each.

The technical problem is further solved by a medical device, in particular for performing a method according to the invention, comprising a first reservoir containing a first fluid medicament and a second reservoir containing a fluid, for example a second fluid medicament, a fluid element connected to said first reservoir and said second reservoir, and a control unit. The control unit is configured to receive information about a desired dose of said first fluid medicament to be ejected. The control unit is further configured to adjust said dose to be ejected from said first reservoir based at least in part on information about a content of the fluid element. Further, the first reservoir, the second reservoir and the fluid element are configured to eject the adjusted dose.

By providing a medical device which is configured such that the dose to be ejected based upon the information about the content of the fluid element is adjusted, the remaining fluid and/or fluid medicament in the fluid elements can be considered during a delivery process, yielding a higher dose accuracies. Moreover no rinsing or flushing of the fluid elements is necessary saving medicaments and power of the medical device. This latter is especially advantageous for portable devices with a limited amount of power.

The control unit can be a logic unit, a microprocessor, for example. The control unit can influence the dose delivery process such that a deviating dose is ejected from the first and/or the second reservoir compared to the user input, for example. Eventually the desired dose will be administered to the user, since the dose to be ejected from the first reservoir and/or from the second reservoir is adjusted based upon information about a content of the fluid element, through which the medicaments are guided.

The ejection of the medicaments from the reservoirs can in particular be performed by electromechanical devices, such as motors, stepper motors or brushless dc motors. These electromechanical devices can move a piston with a bung in order to eject the fluid medicaments from the reservoirs. It is preferred when the reservoirs are provided with an electromechanical device each.

The user preferably provides a desired dose of only one of the medicaments, while the dose of the other medicament is calculated by the control unit, for example. The resulting total dose can then be adjusted by the medical device.

According to an embodiment of the medical device according to the invention, the medical device is a portable medical device, in particular a pen for injecting insulin or an infusion pump. Especially portable devices may lack a precise dosing behavior since less space is available, lower power consumption is demanded and the devices are exposed to agitation and joints, for example. It is especially advantageous to provide a more reliable and more precise dosing behavior of portable devices, while at the same time no significant increase in power consumption and no major changes to the design are necessary.

It is preferred that the medical device further comprises a memory unit. The memory unit can be used to save information such as information about previous ejections and/or temperature data and/or the elapsed time since the last ejection and/or other data of the device history relevant for the determination of the content of the fluid element. The memory unit can also contain the look-up table, for example. Thus, a simple way of providing access to relevant information necessary to increase the dose accuracy is provided.

The medical device can in particular comprise a timing unit, in order to measure the time since the last ejection, for example. The medical device may further comprise a motion detector in form of an accelerometer, for example, to provide information about the movement or agitation of the medical device. These components in particular help to estimate the diffusion process of the content of the fluid element.

It is further preferred, when the fluid element comprises fluidic channels and/or a fluidic chamber, such as a mixing chamber. Fluidic channels can be flexibly designed according to the demand and provide a secure way of guiding a medicament to the injection site or a needle, for example, without using up too much space and creating too much dead volume. This supports a higher dose accuracy. By providing a mixing chamber, the different medicaments being ejected from the reservoirs can be mixed, and a better controlled mixing behavior can be achieved. Moreover a fluidic chamber can provide space for further components such as a needle to be connected, which is in particular inserted into the fluid element.

It is especially preferred when the fluid element comprises valves, in particular a valve for each reservoir. Thus mixing of the medicaments can be prevented up to the valve. In a post-valve mixing chamber a better controlled or predictable mixing of the medicaments can take place.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
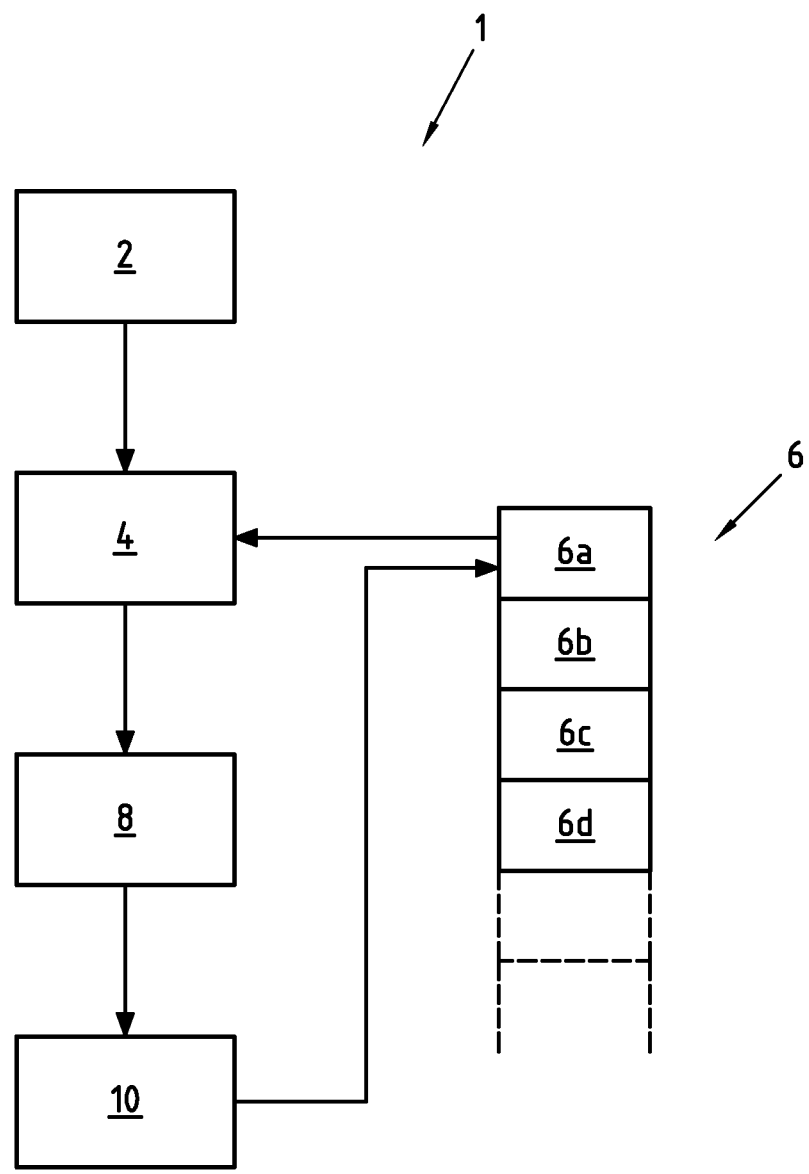
FIG. 1 illustrates a schematic diagram exemplifying an embodiment of the method according to the invention.
Figure 4:
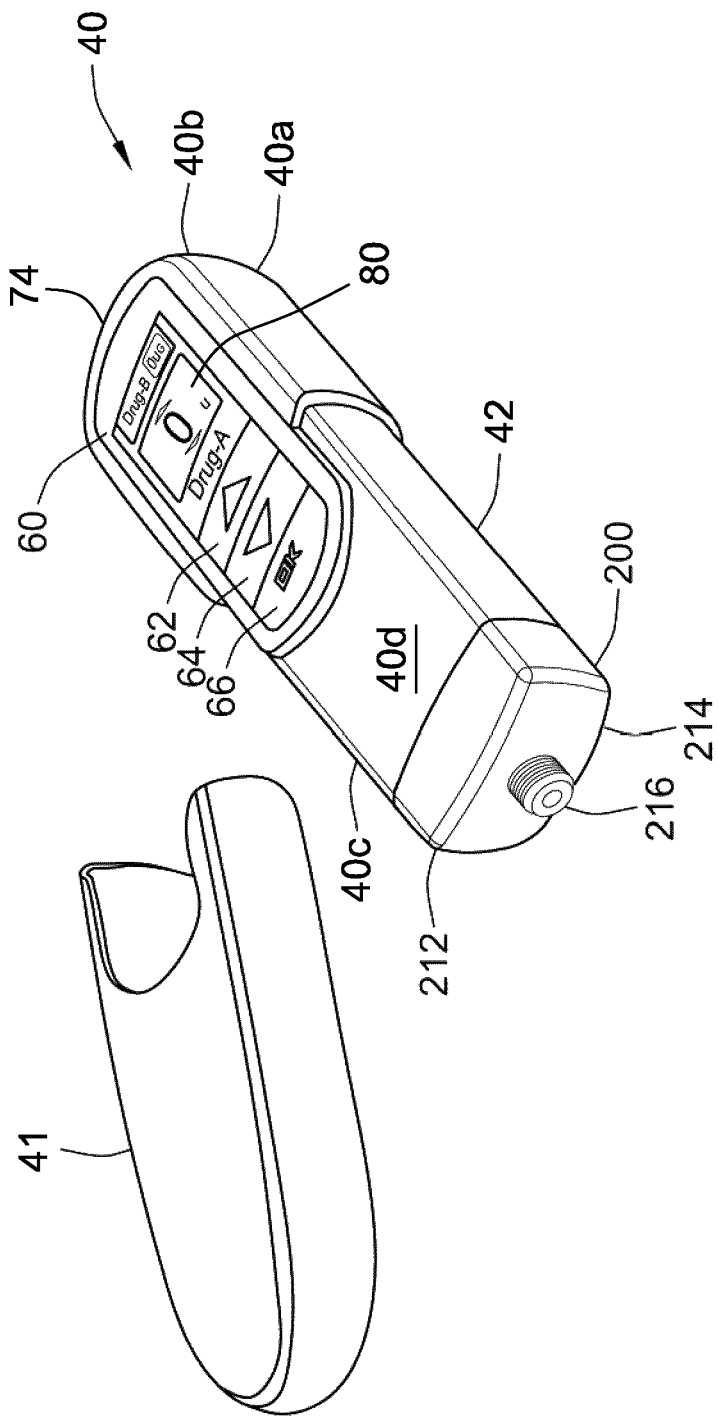
FIG. 4 illustrates a perspective view of a delivery device with an end cap of the device removed.
Figure 6:
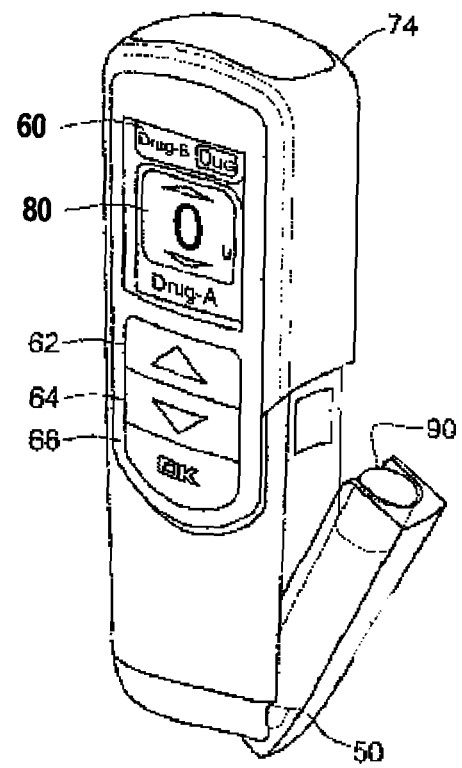
FIG. 6 illustrates a perspective view of the delivery device illustrated in FIG. 4 or 5 with one cartridge retainer in an open position.

FIG. 1 illustrates a schematic diagram 1 exemplifying an embodiment of the method according to the invention. The first step 2 is to receive information about a desired dose which may be provided by a user, by another computational unit or by a memory unit, for example. The user may use an interface in form of dose setting buttons 62, 64, 66, as illustrated in FIGS. 4 and 6. To provide a more accurate dose, the relevant information 6 about the content of a fluid element 18 connected to a first reservoir 14 and a second reservoir 16 (confer FIG. 2a) is taken into account in step 4. This information 6 can comprise information such as: dose information 6a of previous ejections from the first and/or second reservoir, time information 6b when the last priming was performed or the elapsed time since the last ejection or use of the device, information 6c about past or current temperatures and/or information 6d about the degree of movement of the medical device 12. These variables will influence the adjustment 8 of the dose to be ejected from the first and/or second reservoir 14, 16. Eventually, the adjusted dose will be ejected in step 10 from the first and/or second reservoir 14, 16 through the fluid element 18, resulting in the desired dose to be delivered. Information about the actually ejected dose from step 10 can be stored to serve as information 6 for adjustment of subsequent deliveries.

Figure 2A:
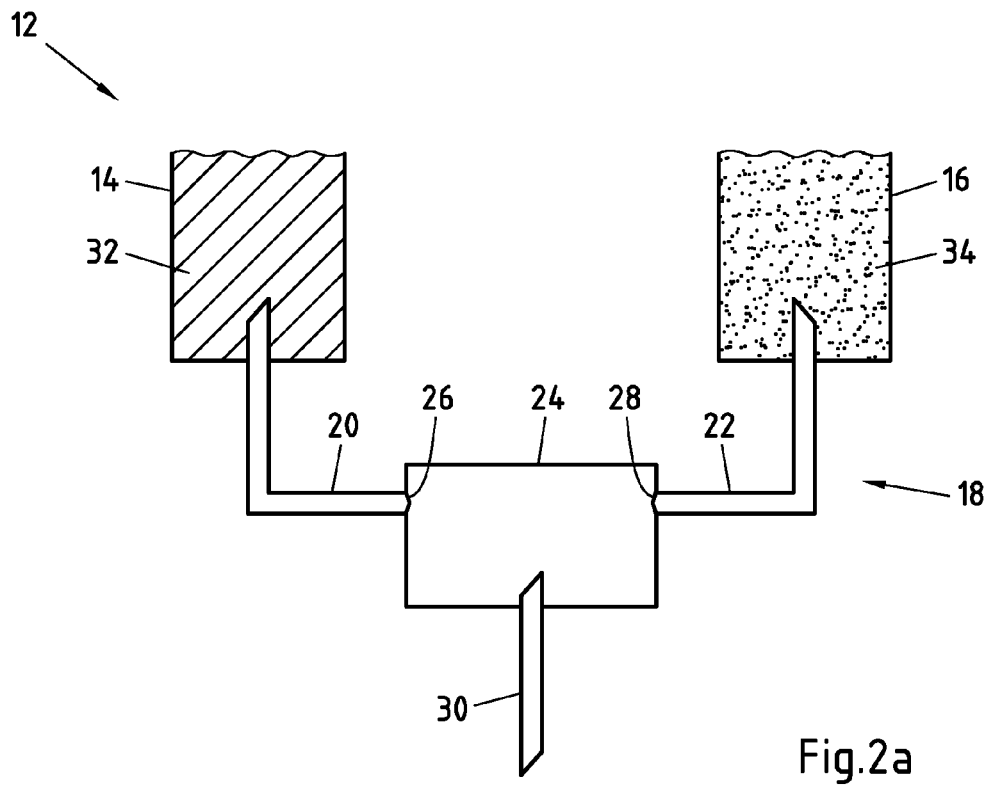
FIG. 2a-e illustrates a medical device with a first reservoir, a second reservoir and a fluid element for different points of time, in particular during a priming process.
Figure 9:
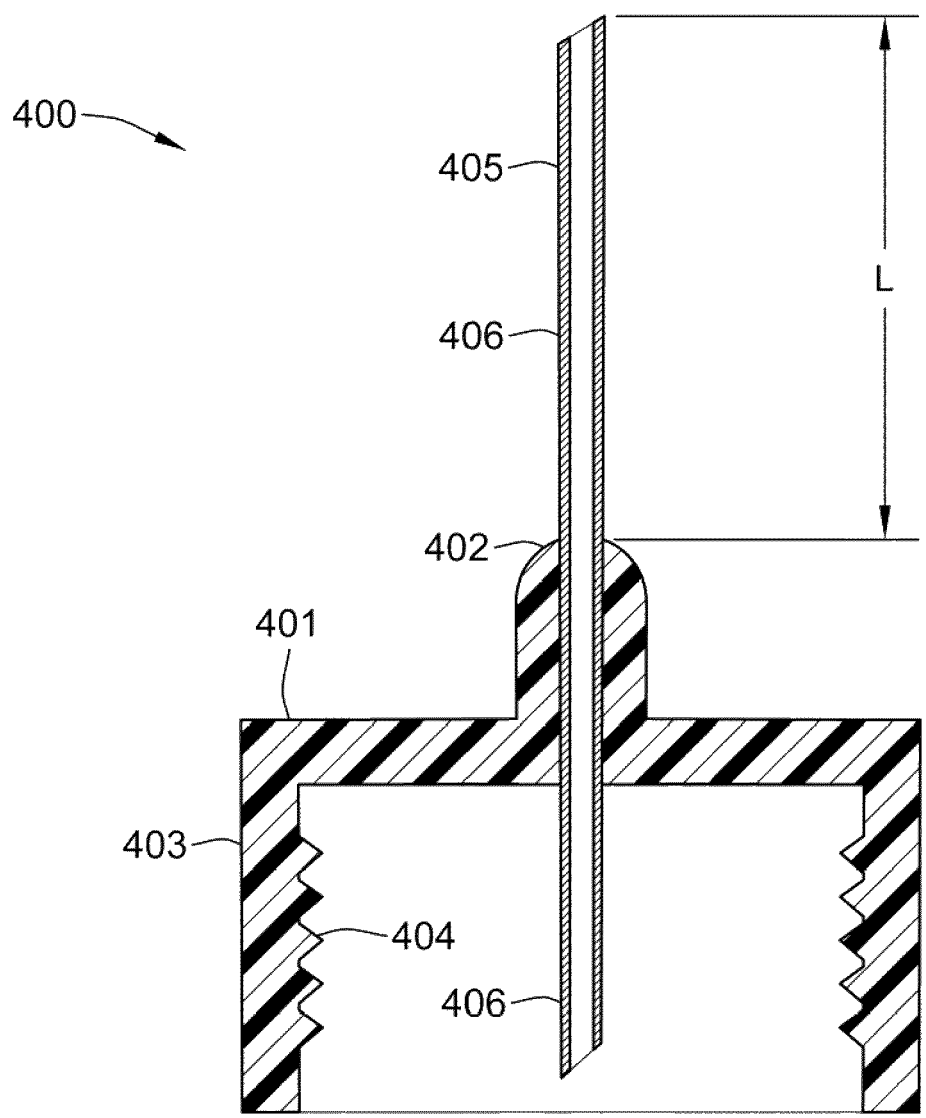
FIG. 9 illustrates one arrangement of a needle assembly that may be mounted on a distal end of the delivery device.
Figure 10:
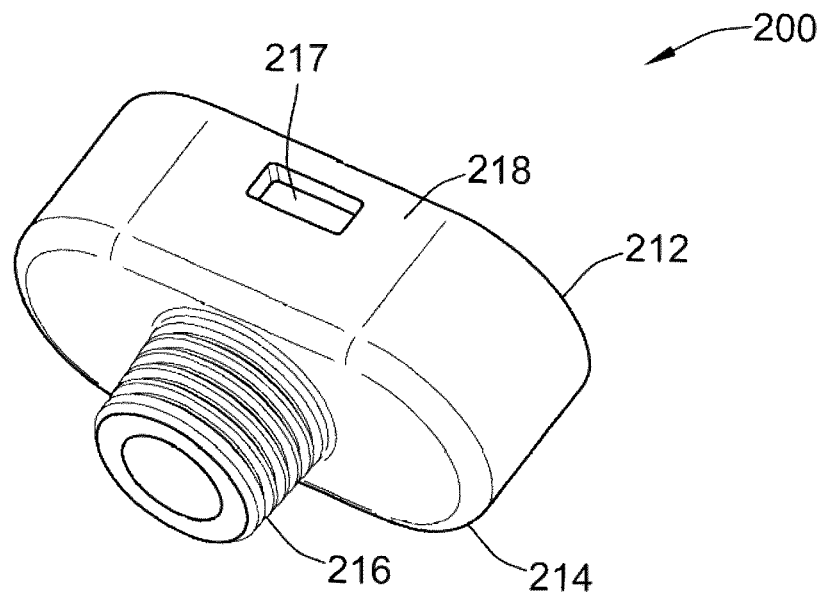
FIG. 10 illustrates a perspective view of the dispense interface illustrated in FIG. 7.
Figure 11:
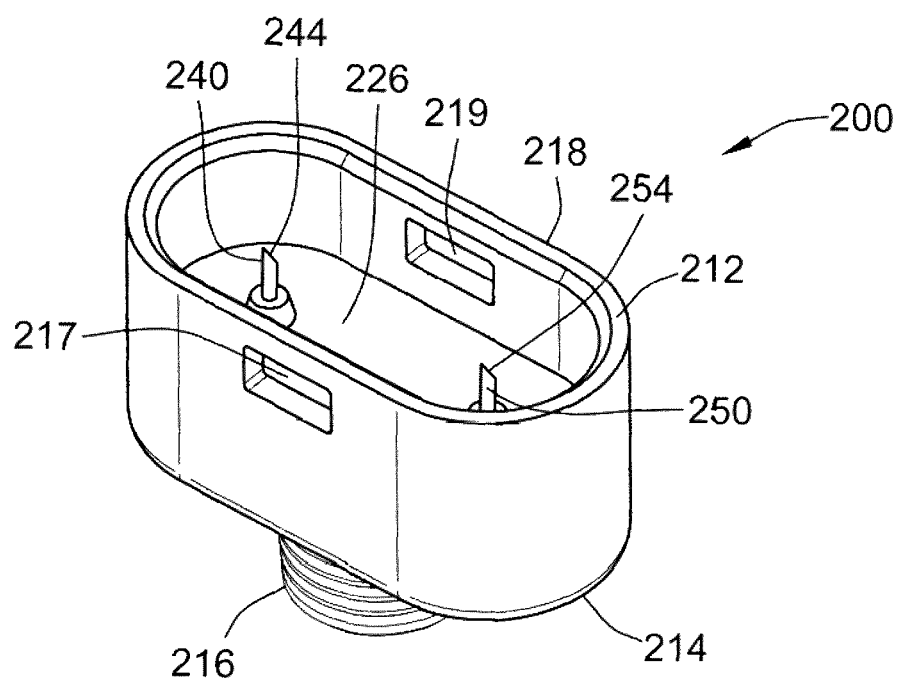
FIG. 11 illustrates another perspective view of the dispense interface illustrated in FIG. 7.

FIG. 2a illustrates a section of a medical device 12, such as the drug delivery device 40 illustrated in FIG. 4, comprising a first reservoir 14 in form of a first cartridge and a second reservoir 16 in form of a second cartridge, such as the cartridges 90, 100 shown in FIG. 11, and a fluid element 18. The fluid element 18 comprises a first channel or fluid groove 20 providing a fluid connection to the first reservoir 14 and a second channel or fluid groove 22 providing a fluid connection to the second reservoir 16. The fluid element 18 further comprises an fluidic chamber 24 similar to the holding chamber 200 as illustrated in FIG. 9. The channels 20, 22 are separated from the fluidic chamber 24 by valves 26, 28. These valves may be opened and closed either mechanically or they may also be operated depending on the pressure within the channels 20, 22. For example, only when the pressure in channel 20 is large enough, the valve 26 opens and the valve 26 is closed otherwise. The fluid element further comprises a double ended needle 30. This needle 30 can be provided by a double ended needle assembly 400 as shown in FIG. 10, for example. The fluid element can in particular be provided by a dispense interface 200 as illustrated in FIG. 9.

The ejection of the medicaments 32, 34 can be initiated by a control unit (not shown), for example. The control unit can then instruct electromechanical devices to exert pressure on the medicaments 32, 34 in the reservoirs 14, 16 in order to force the medicaments 32, 34 downstream through the fluid element 18. Preferably, the medicaments 32, 34 can be ejected independently from each other.

The first reservoir 14 contains a first medicament 32, while the second reservoir 16 contains a second medicament 34. The fluid element 18 does not contain any fluid or medicaments yet. This can especially be the case, when the fluid element is exchanged together with the dispense interface 200, for example. In this case a first priming will usually take place. A priming substantially comprises the steps of ejecting a small amount of each of the medicaments.

Figure 2B:
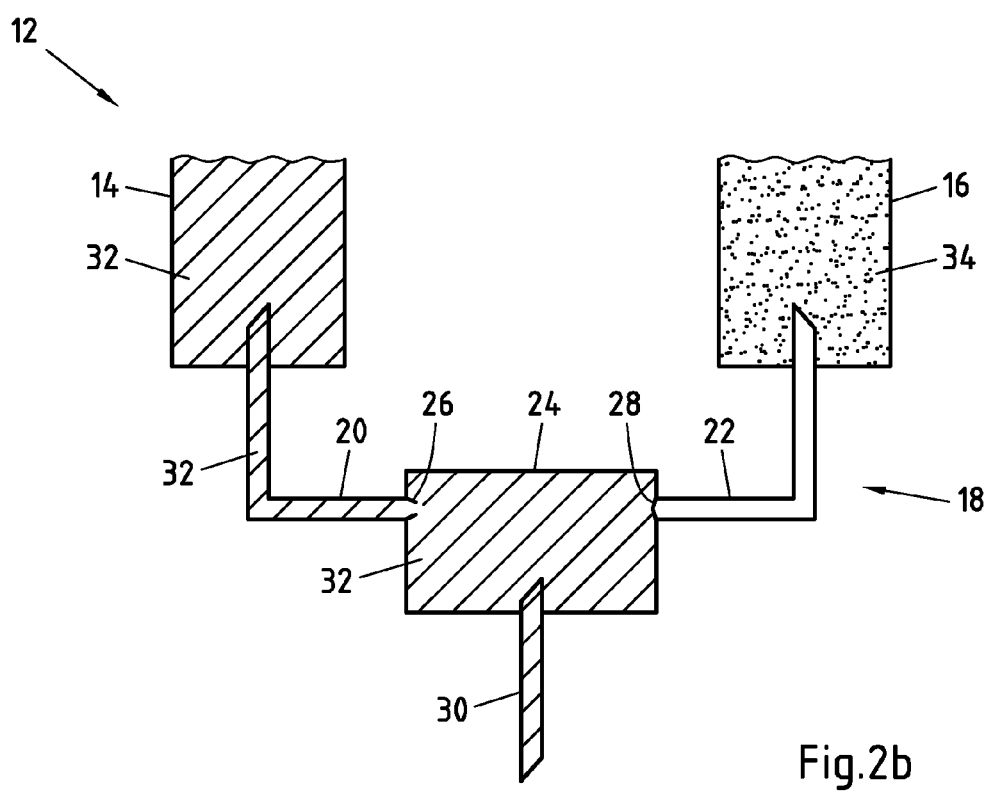

FIG. 2b shows the device illustrated in FIG. 2a after a dose of the first medicament 32 is ejected from the reservoir 14. The medicament 32 substantially fills the channel 20, the fluidic chamber 24 and the needle 30. An advancement of the medicament 32 into the channel 22 is prevented by the valve 28.

Figure 2C:
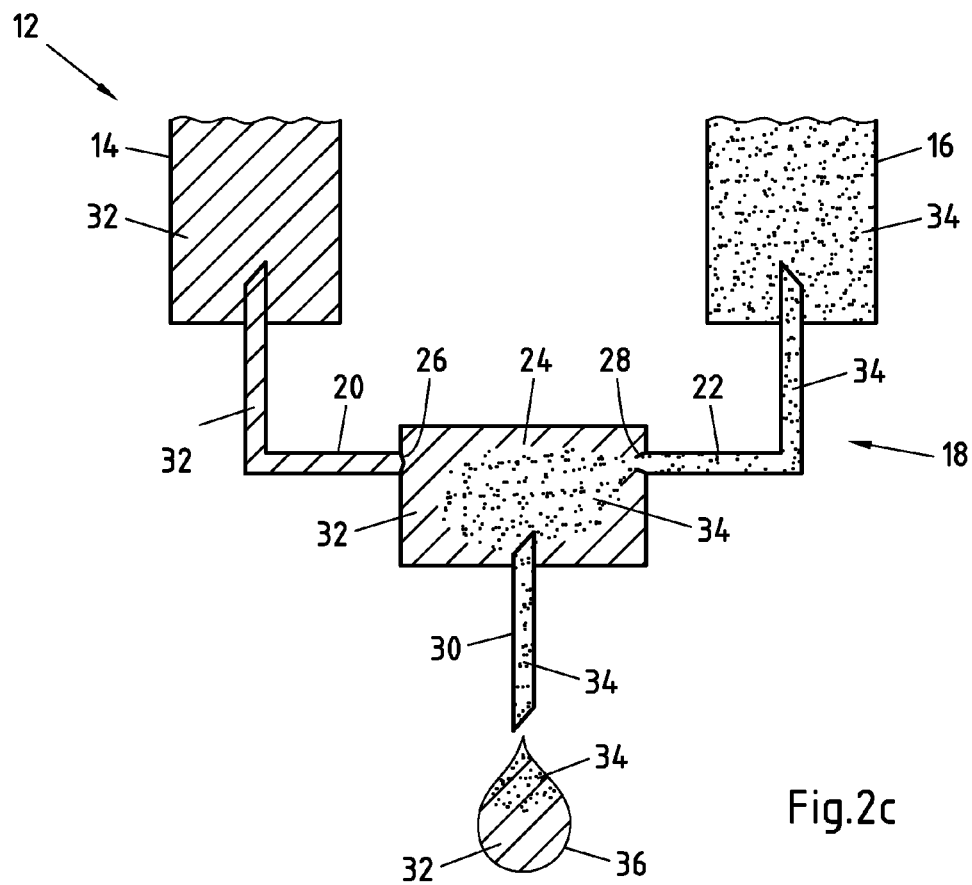

FIG. 2c shows the state of the device 12 directly after an ejection of the medicament 34 from the reservoir 16. As can be seen, the channel 22 is filled with the second medicament 34. The second medicament has partially pushed the first medicament 32 aside, meaning out of the device 12 through the needle 30. The drop 36 substantially contains the medicament 32, but it also comprises small amounts of the medicament 34 in this case. As can be further seen from FIG. 2c, there are remainders of the medicament 32 within the fluid element 18, in particular in the fluidic chamber 24. Directly after the ejection of the medicament 34, the medicament 32 is concentrated in areas, where the fluid flow of the second medicament 34 was weaker; in this case at the borders and the corners of the fluidic chamber 24. At this point a first priming process is completed. The order of the medicaments being ejected may be the other way around, of course, or there may also be more than two medicaments used in the medical device 12.

Of course, a priming process can not only be performed when the fluid element 18 is empty, as illustrated in FIG. 2a, but also when the fluid element 18 already contains fluids due to dose deliveries, for example. With the process of priming, the device 12 can substantially be brought into the known state 2c, since this state is approximately independent of earlier states of the content of the fluid element 18, since the fluid element 18 is rinsed by the priming process.

If, at this point in time, a second ejection of the second medicament 34 would be performed, for instance in order to administer the second medicament 32, only a low contamination with the first medicament would be observed. If on the other hand, an ejection of the first medicament 32 would be performed, the ejected dose would comprise a high amount of the second medicament 34. Thus the doses to be ejected from the reservoirs 14, 16 are adjusted accordingly providing a higher dose accuracy in the delivered dose.

The situation illustrated in FIG. 2c does not only occur after a priming process, but also after a regular dose delivery. Then the ratio and distribution of the first medicament 32 and second medicament 34 in the fluidic chamber 24 depends upon the dose delivered during the dose delivery and the order of the medicaments delivered. Of course, during a dose delivery only a single medicament can be administered, as well.

Figure 2D:
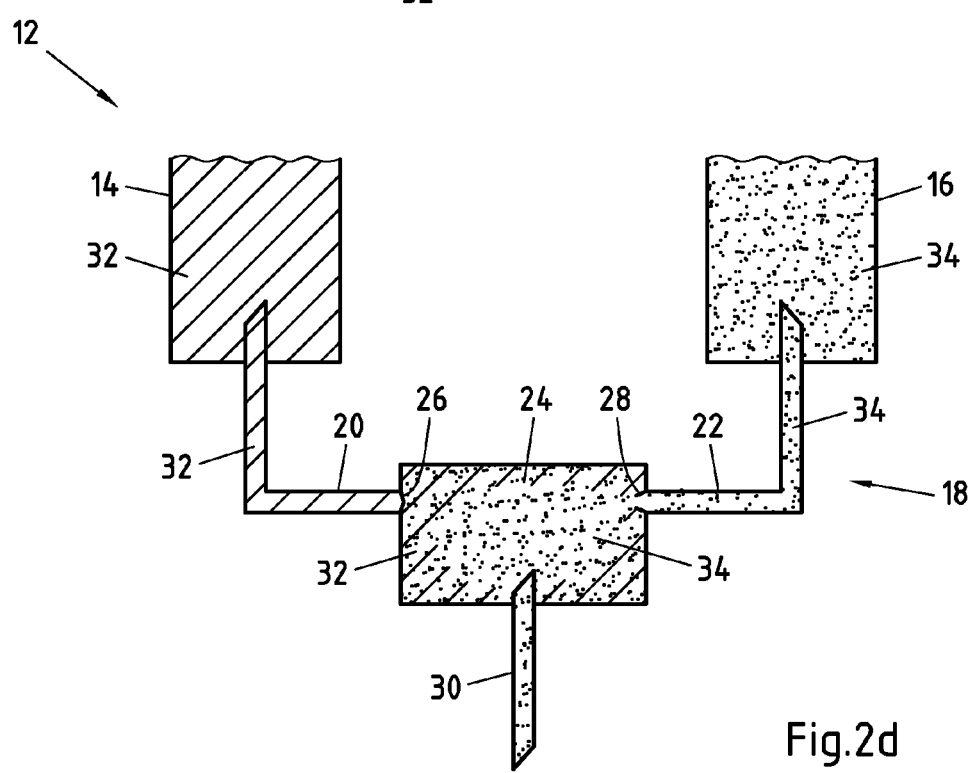

FIG. 2d shows the device 12 from FIG. 2c after a first period of time. Due to the valves, the channels 20, 22 and the reservoirs 14, 16 are not contaminated by the respective other medicament 32, 34. However, in the fluidic chamber 24 a intermixing of the first medicament 32 with the second medicament 34 takes place. This is caused mainly by diffusion processes. These diffusion processes can be influenced by properties of the fluids, such as viscosity, by the temperature, by the shape of the fluid element 18 and/or by agitation of the medical device 12 and the fluid element 18. It is apparent, that when the first medicament 32 or second medicament 34 is ejected, the dose delivered through the needle 30 will show a higher content of the first medicament 32 as compared to a dose delivered at an earlier point in time, as illustrated in FIG. 2c.

Figure 2E:
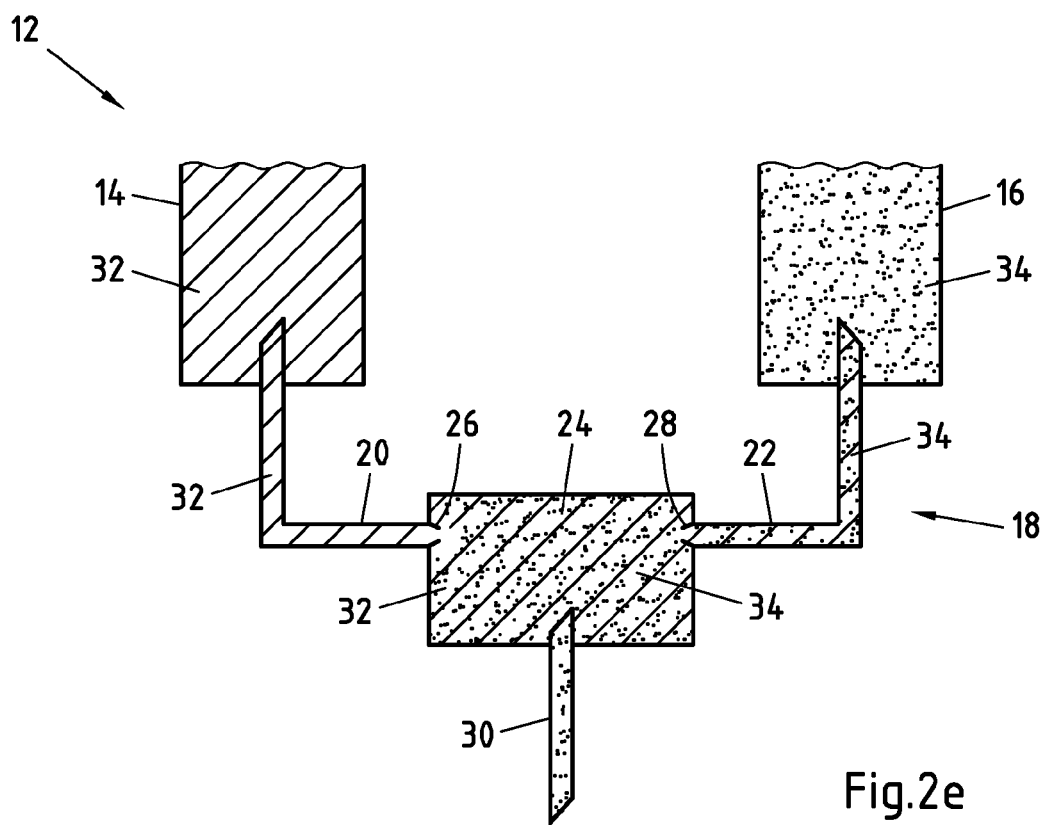

FIG. 2e shows the device 12 from FIG. 2c after a second period of time, larger than the first period of time. The intermixing of the first medicament 32 with the second medicament 34 in the area of the fluidic chamber 24 has advanced, further increasing the dose of the first medicament 32 being ejected through the needle 30 in case of a dose delivery. Especially in comparison with the state of the content of the fluid element 18 shown in FIG. 2c, it is apparent that the time interval between a priming process or a dose delivery and a further dose delivery would affect the dose ejected through the needle 30. By taking into account the content of the fluid element 18, an according adjustment of the doses ejected from the first and/or second reservoirs can be provided.

Figure 3:
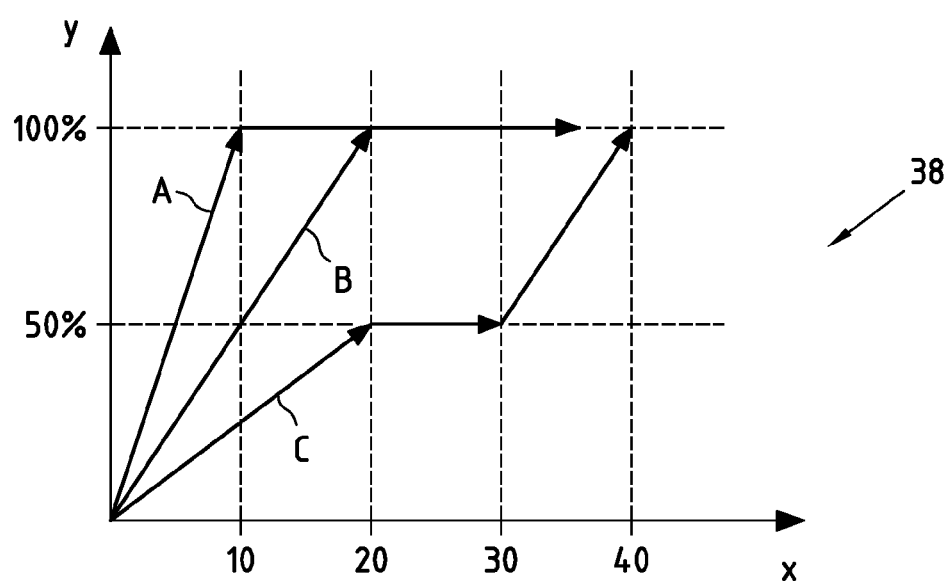
FIG. 3 illustrates a diagram with different scenarios of delivering doses of the first and the second medicament.

FIG. 3 illustrates a diagram 38 with different scenarios of delivering doses of the first medicament 32 and the second medicament 34. In this case, both the first and second medicament contain a first drug "x", while the second medicament also contains a second drug "y". In this example, it is desired that the user receives a complete dose of 100% of the second drug y, the dose of which is illustrated on the y-axis in percent. Additionally, the user should be able to receive the first drug "x" in varying doses through out the day. The amount of the second drug "x" is illustrated on the x-axis of the diagram 38 in units, a standard measure for insulin doses. In this case the second drug "y" can only be administered together with the first drug "x", since the second medicament contains both. The dose of drug "x" can in particular be chosen by the user, while drug "y" is preferably a fixed dose per day.

In the first scenario, illustrated by the path A in FIG. 3, the user chooses to administer 10 units of drug "x". At the same time the 100% dose of drug "y" is administered. The doses of the first and second medicament are automatically determined by a control unit, for instance.

If the mixing ratio of the drugs "x"/"y" in the second medicament is for example 10 units of "x" to a 100%-dose of "y", the 10 units of drug "x" would be the minimum dose at which it would still be possible to administer a complete 100%-dose of drug "y". In this case the dose would only consist of the second medicament.

Afterward the user can administer arbitrary doses of the first drug "x", which would be realized by delivering the first medicament only. This results in a horizontal path in diagram 38.

In the second scenario, illustrated by path B in FIG. 3, in contrast to the first scenario, the user chooses to administer 20 units of drug "x". In that case the control unit can automatically set the ratio of the first medicament, which only contains drug "x", and the second medicament appropriately, so that a dose of 100% drug "y" and 20 unit of drug "x" will be delivered to the user.

In the third scenario, illustrated by path C in FIG. 3, the user chooses to first administer 20 units of drug "x". In contrast to the first and second scenario, the dose of drug "y" is only set to 50%. This may be done by the user or automatically by the control unit, when the dose of drug "y" should be split into a dose in the morning and the evening, for example. Afterwards, 10 units of only drug "x" are ejected, that means that only the first medicament is administered. Subsequently, the user chooses to administer 10 units of drug "x", while at the same time the remaining 50% of the drug "y" are administered.

As can be seen from these scenarios, the dosing needs to be as precise as possible, while at the same time flexible dosing needs to be feasible. The dosing accuracy is significantly improved in such scenarios, when information about the content of the fluid element 18 is taken into account.

In connection with the following figures, components and embodiments of drug delivery devices are described. The use of a method according to the invention and of a medical device according to the invention in connection with the described exemplary embodiments is in particular advantageous, since accurate dosing is of particular importance in connection with these devices.

The drug delivery device 40 illustrated in FIG. 4 comprises a main body 40a that extends from a proximal end 40b to a distal end 40c. At the distal end 40c, a removable end cap or cover 41 is provided. This end cap 41 and the distal end 40c of the main body 40a work together to provide a snap fit or form fit connection so that once the cover 41 is slid onto the distal end 40c of the main body 40a, this frictional fit between the cap and the main body outer surface 40*d* prevents the cover from inadvertently falling off the main body.

The main body 40*a* contains a micro-processor control unit, an electro-mechanical drive train, and at least two medicament reservoirs. When the end cap or cover 41 is removed from the device 40 (as illustrated in FIG. 4), a dispense interface 200 is mounted to the distal end 40*c* of the main body 40*a*, and a dose dispenser (e.g., a needle assembly) is attached to the interface. The drug delivery device 40 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 40*a*, so that the empty cartridge can be removed and a new cartridge can be inserted.

A control panel region 60 is provided near the proximal end of the main body 40*a*. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 4).

The cartridge holder 42 can be removably attached to the main body 40*a* and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 42, the drug delivery device illustrated in FIG. 4 includes a dispense interface 200. As will be described in relation to FIG. 7, in one arrangement, this dispense interface 200 includes a main outer body 212 that is removably attached to a distal end 43 of the cartridge housing 42. As can be seen in FIG. 4, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 40.

Once the device is turned on, the digital display 80 shown in FIG. 4 illuminates and provides the user certain device information, preferably information relating to the medicaments contained within the cartridge holder 42. For example, the user is provided with certain information relating to both the primary medicament (Drug A) and the secondary medicament (Drug B).

As shown in FIG. 6, the first and second cartridge retainers 50, 52 may be hinged cartridge retainers. These hinged retainers allow user access to the cartridges. FIG. 6 illustrates a perspective view of the cartridge holder 42 illustrated in FIG. 4 with the first hinged cartridge retainer 50 in an open position. FIG. 6 illustrates how a user might access the first cartridge 90 by opening up the first retainer 50 and thereby having access to the first cartridge 90.

Figure 7:
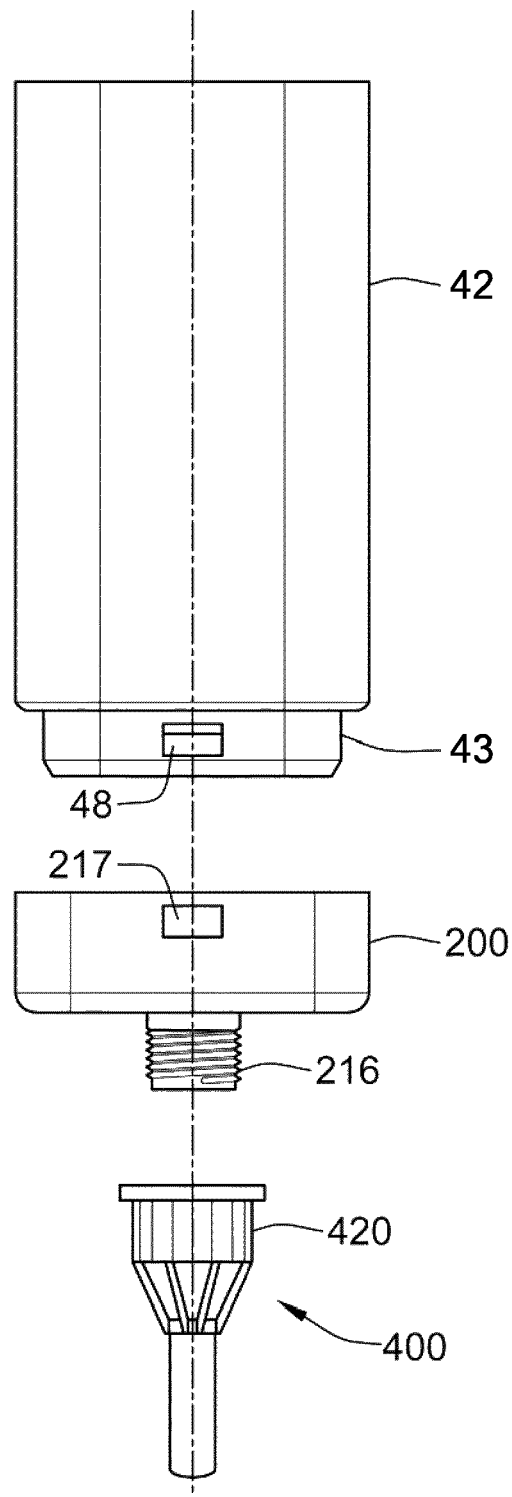
FIG. 7 illustrates a dispense interface and a dose dispenser that may be removably mounted on a distal end of the delivery device illustrated in FIG. 4.

As mentioned above when discussing FIG. 4, a dispense interface 200 is coupled to the distal end of the cartridge holder 42. FIG. 7 illustrates a flat view of the dispense interface 200 unconnected to the distal end of the cartridge holder 42. A dose dispenser or needle assembly that may be used with the interface 200 is also illustrated and is provided in a protective outer cap 420.

Figure 8:
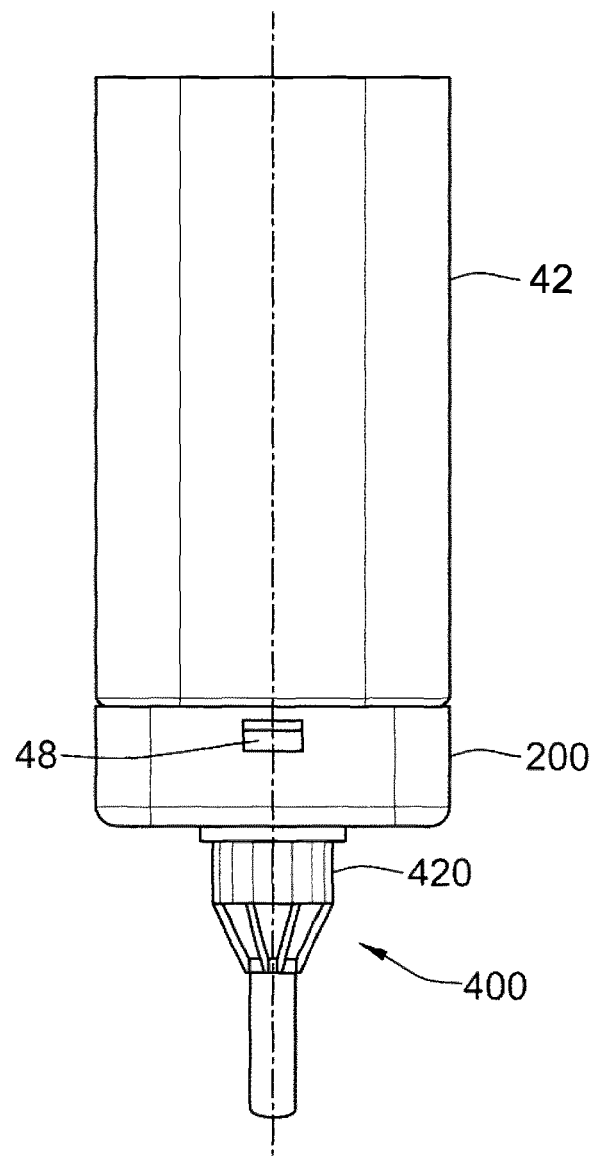
FIG. 8 illustrates the dispense interface and the dose dispenser illustrated in FIG. 7 mounted on a distal end of the delivery device illustrated in FIG. 4.

In FIG. 8, the dispense interface 200 illustrated in FIG. 7 is shown coupled to the cartridge holder 42. The axial attachment means between the dispense interface 200 and the cartridge holder 42 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

FIG. 8 also illustrates the needle assembly 400 and protective cover 420 coupled to the distal end of the dispense interface 200 that may be screwed onto the needle hub of the interface 200. FIG. 9 illustrates a cross sectional view of the double ended needle assembly 402 mounted on the dispense interface 200 in FIG. 8.

The needle assembly 400 illustrated in FIG. 9 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 7 and 8 provides a form fit around the outer surface 403 of the hub 401.

Referring now to FIGS. 7 to 14, one preferred arrangement of this interface 200 will now be discussed. In this one preferred arrangement, this interface 200 comprises:
 a. a main outer body 210,
 b. an first inner body 220,
 c. a second inner body 230,
 d. a first piercing needle 240,
 e. a second piercing needle 250,
 f. a valve seal 260, and
 g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 42. Preferably, the connecting member is configured so as to allow the dispense interface 200 to be removably connected the cartridge holder 42. In one preferred interface arrangement, the proximal end of the interface 200 is configured with an upwardly extending wall 218 having at least one recess. For example, as may be seen from FIG. 11, the upwardly extending wall 218 comprises at least a first recess 217 and a second recess 219.

Figure 5:
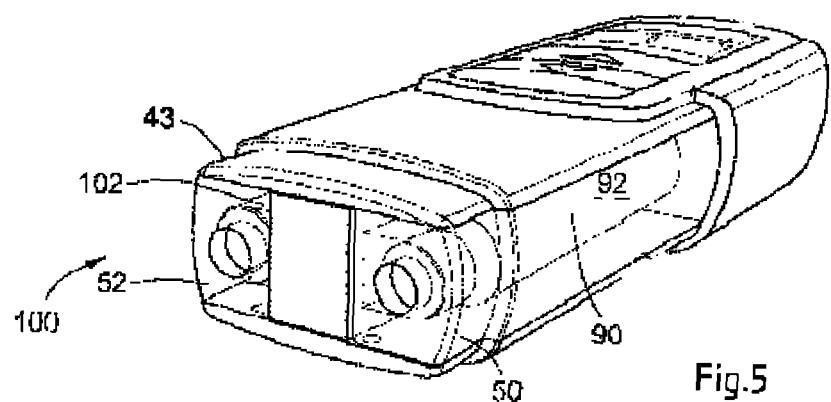
FIG. 5 illustrates a perspective view of the delivery device distal end showing the cartridge.

Preferably, the first and the second recesses 217, 219 are positioned within this main outer body wall so as to cooperate with an outwardly protruding member located near the distal end of the cartridge housing 40 of the drug delivery device 40. For example, this outwardly protruding member 48 of the cartridge housing may be seen in FIGS. 7 and 5. A second similar protruding member is provided on the opposite side of the cartridge housing. As such, when the interface 200 is axially slid over the distal end of the cartridge housing 42, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 42 to be axially coupled could be used as well.

The main outer body 210 and the distal end of the cartridge holder 42 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 9. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 11-14. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 12, the extending wall 218 of the main outer body 210 is provided with a first rib 213a and a second rib 213b. This first rib 213a is also illustrated in FIG. 13. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 12:
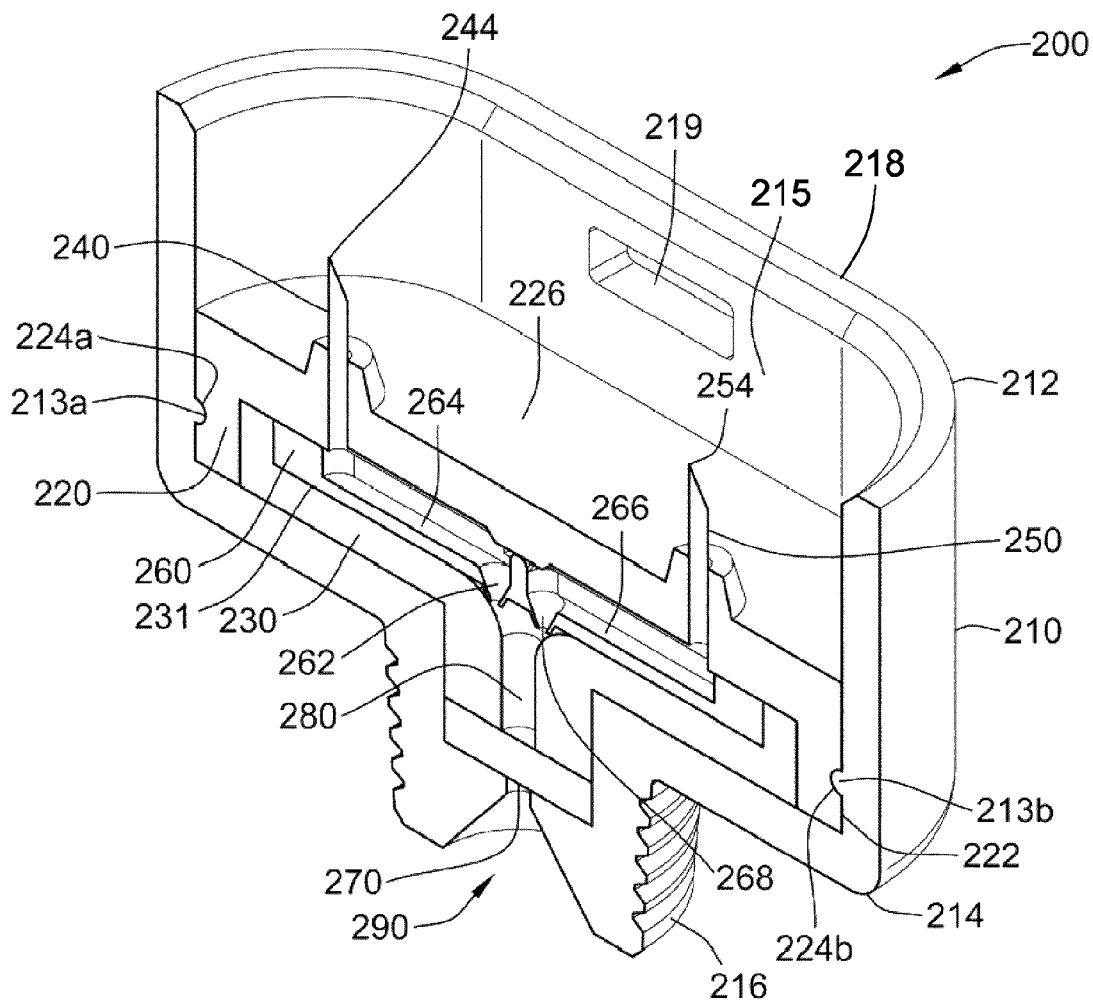
FIG. 12 illustrates a cross-sectional view of the dispense interface illustrated in FIG. 7.
Figure 13:
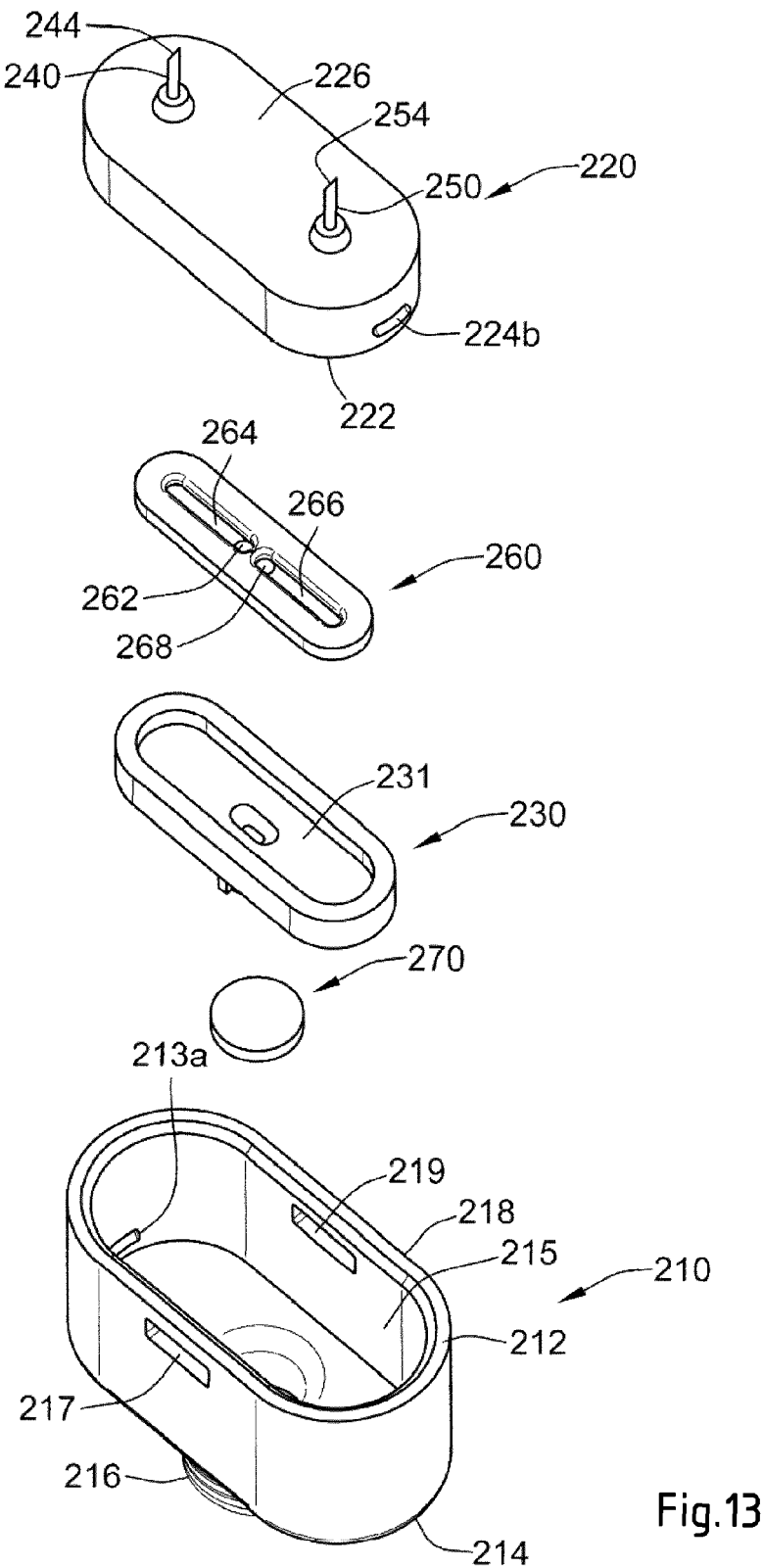
FIG. 13 illustrates an exploded view of the dispense interface illustrated in FIG. 7

In addition, as can be seen in FIG. 11-13, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 12 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 9), the output fluid path allows both medicaments to be in fluid communication with the attached needle assembly.

The hub interface 200 further comprises a second inner body 230. As can be seen from FIG. 12, this second inner body 230 has an upper surface that defines a recess, and the valve seal 260 is positioned within this recess. Therefore, when the interface 200 is assembled as shown in FIG. 12, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 14:
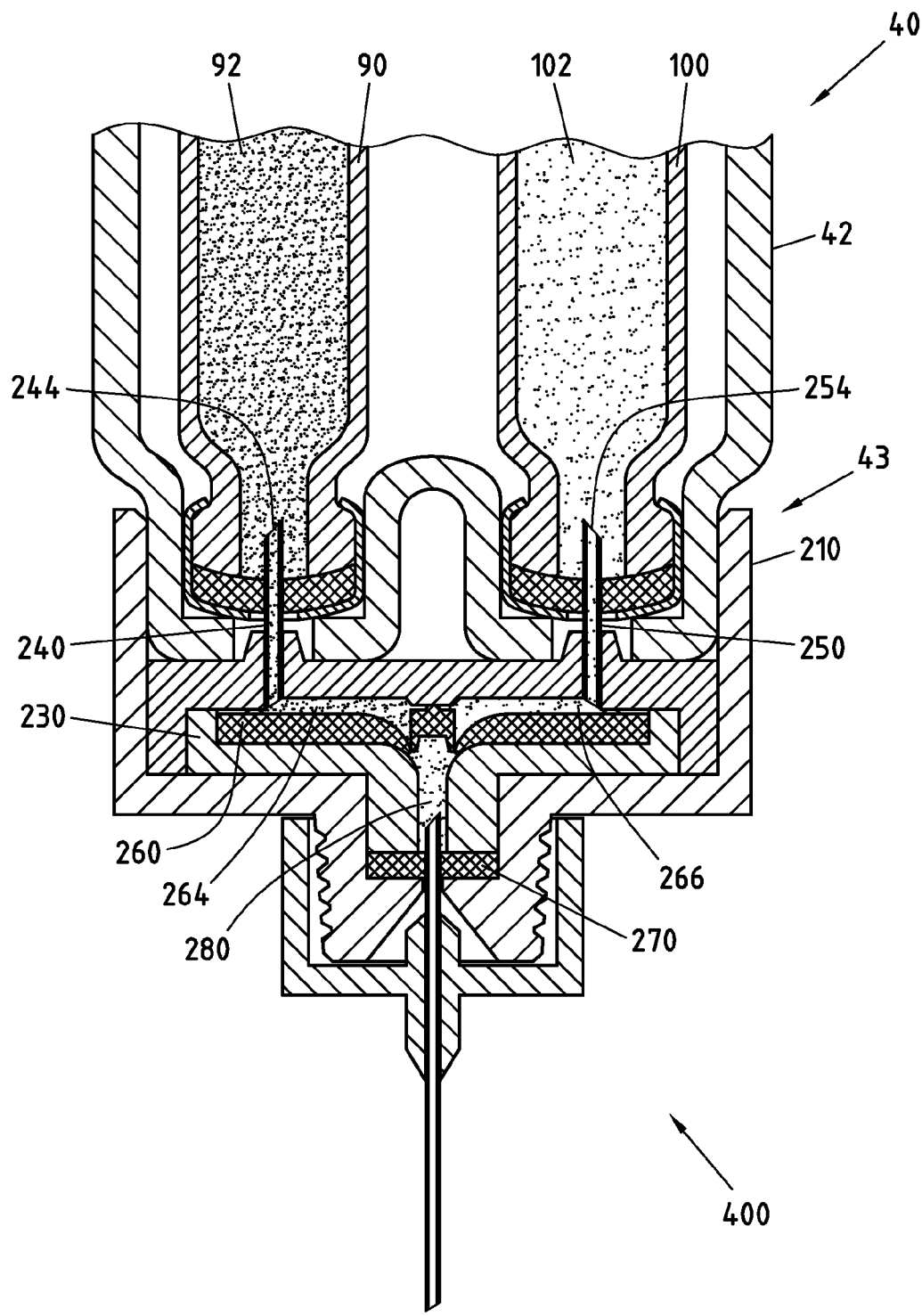
FIG. 14 illustrates a cross-sectional view of the dispense interface and needle assembly mounted onto a drug delivery device, such as the device illustrated in FIG. 4.

FIG. 14 illustrates the dispense interface 200 after it has been mounted onto the distal end 43 of the cartridge holder 42 of the drug delivery device 40 illustrated in FIG. 4. A double ended needle 400 is also mounted to the distal end of this interface. The cartridge holder 42 is illustrated as having a first cartridge containing a first medicament and a second cartridge containing a second medicament.

When the interface 200 is first mounted over the distal end of the cartridge holder 42, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 14 illustrates a preferred arrangement of such a dispense interface 200 that is coupled to a distal end 40c of the main body 40a of drug delivery device 40. Preferably, such a dispense interface 200 is removably coupled to the cartridge holder 42 of the drug delivery device 40.

As illustrated in FIG. 14, the dispense interface 200 is coupled to the distal end of a cartridge housing 40. This cartridge holder 42 is illustrated as containing the first cartridge 90 containing the primary medicament 92 and the second cartridge 100 containing the secondary medicament 102. Once coupled to the cartridge housing 4042 the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 14, once the dispense interface 200 is attached to the cartridge holder 42, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl -LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28]Exendin-4(1-39),
des Pro36 [IsoAsp28]Exendin-4(1-39),
des Pro36 [Met(O)14, Asp28]Exendin-4(1-39),
des Pro36 [Met(O)14, IsoAsp28]Exendin-4(1-39),
des Pro36 [Trp(O2)25, Asp28]Exendin-4(1-39),
des Pro36 [Trp(O2)25, IsoAsp28]Exendin-4(1-39),
des Pro36 [Met(O)14 Trp(O2)25, Asp28]Exendin-4(1-39),
des Pro36 [Met(O)14 Trp(O2)25, IsoAsp28]Exendin-4(1-39); or des Pro36 [Asp28]Exendin-4(1-39),
des Pro36 [IsoAsp28]Exendin-4(1-39),
des Pro36 [Met(O)14, Asp28]Exendin-4(1-39),
des Pro36 [Met(O)14, IsoAsp28]Exendin-4(1-39),
des Pro36 [Trp(O2)25, Asp28]Exendin-4(1-39),
des Pro36 [Trp(O2)25, IsoAsp28]Exendin-4(1-39), des Pro36 [Met(O)14 Trp(O2)25, Asp28]Exendin-4(1-39), des Pro36 [Met(O)14 Trp(O2)25, IsoAsp28]Exendin-4(1-39), wherein the group -Lys6-NH2 may be bound to the C-terminus of the Exendin-4 derivative;

or an Exendin-4 derivative of the sequence

H-(Lys)6-des Pro36 [Asp28]Exendin-4(1-39)-Lys6-NH2, des Asp28 Pro36, Pro37, Pro38Exendin-4(1-39)-NH2, H-(Lys)6-des Pro36, Pro38 [Asp28]Exendin-4(1-39)-NH2, H-Asn-(Glu)5des Pro36, Pro37, Pro38 [Asp28]Exendin-4(1-39)-NH2, des Pro36, Pro37, Pro38 [Asp28]Exendin-4(1-39)-(Lys)6-NH2, H-(Lys)6-des Pro36, Pro37, Pro38 [Asp28]Exendin-4(1-39)-(Lys)6-NH2, H-Asn-(Glu)5-des Pro36, Pro37, Pro38 [Asp28]Exendin-4(1-39)-(Lys)6-NH2, H-(Lys)6-des Pro36 [Trp(O2)25, Asp28]Exendin-4(1-39)-Lys6-NH2, H-des Asp28 Pro36, Pro37, Pro38 [Trp(02)25]Exendin-4(1-39)-NH2, H-(Lys)6-des Pro36, Pro37, Pro38 [Trp(O2)25, Asp28]Exendin-4(1-39)-NH2, H-Asn-(Glu)5-des Pro36, Pro37, Pro38 [Trp(O2)25, Asp28]Exendin-4(1-39)-NH2, des Pro36, Pro37, Pro38 [Trp(O2)25, Asp28]Exendin-4(1-39)-(Lys)6-NH2, H-(Lys)6-des Pro36, Pro37, Pro38 [Trp(O2)25, Asp28]Exendin-4(1-39)-(Lys)6-NH2, H-Asn-(Glu)5-des Pro36, Pro37, Pro38 [Trp(O2)25, Asp28]Exendin-4(1-39)-(Lys)6-NH2, H-(Lys)6-des Pro36 [Met(O)14, Asp28]Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28]Exendin-4(1-39)-NH2, H-Asn-(Glu)5-des Pro36, Pro37, Pro38 [Met(O)14, Asp28]Exendin-4(1-39)-NH2, des Pro36, Pro37, Pro38 [Met(O)14, Asp28]Exendin-4(1-39)-(Lys)6-NH2, H-(Lys)6-des Pro36, Pro37, Pro38 [Met(O)14, Asp28]Exendin-4(1-39)-(Lys)6-NH2, H-Asn-(Glu)5 des Pro36, Pro37, Pro38 [Met(O)14, Asp28]Exendin-4(1-39)-(Lys)6-NH2, H-Lys6-des Pro36 [Met(O)14, Trp(O2)25, Asp28]Exendin-4(1-39)-Lys6-NH2, H-des Asp28 Pro36, Pro37, Pro38 [Met(O)14, Trp(02)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28]Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28]Exendin-4(S1-39)-(Lys)6-NH2, H-Asn-(Glu)5-des Pro36, Pro37, Pro38 [Met(O)14, Trp(O2)25, Asp28]Exendin-4(1-39)-(Lys)6-NH2;

or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A method for delivering at least one fluid medicament from a medical device comprising a first reservoir containing a first fluid medicament, a second reservoir containing a second fluid, a fluid element connected to said first reservoir and said second reservoir and through which said first fluid medicament is to be ejected, and a control unit, the method comprising:
   receiving, by the control unit, information about a desired dose of said first fluid medicament to be ejected,
   in response to receiving the information about the desired dose of said first fluid medicament, the control unit receiving information about a content of said fluid element,
   wherein the information about said content of said fluid element comprises at least one of an amount of first fluid medicament remaining in the fluid element after a previous ejection from said first reservoir and an amount of second fluid remaining in the fluid element after a previous ejection from said second reservoir,
   automatically adjusting said desired dose to an adjusted dose to be ejected from said first reservoir based at least in part on said information about the content of said fluid element, wherein the adjustment is performed by the control unit, and
   ejecting said adjusted dose from said first reservoir through said fluid element.

2. The method according to claim 1, wherein information about said content of said fluid element is also based at least in part on a last priming and subsequent ejections.

3. The method according to claim 1, wherein information about said content of said fluid element is also based at least in part on a time elapsed since a last ejection.

4. The method according to claim 1, wherein information about said content of said fluid element is also based at least in part on a temperature of said medical device.

5. The method according to claim 1, wherein information about said content of said fluid element is also based at least in part on a movement of said medical device.

6. The method according to claim 1, wherein information about said content of said fluid element is also based at least in part on properties of the first fluid medicament and/or the second fluid.

7. The method according to claim 1, wherein said information about said content of said fluid element is also determined based at least in part on calculation.

8. The method according to claim 1, wherein said medicament of said first reservoir and said second fluid of said second reservoir are ejected one after another.

9. The method according to claim 1, wherein said second fluid in said second reservoir contains a mixture of said first fluid medicament and a second medicament.

10. The method according to claim 1, further comprising:
    ejecting a supplementary dose of said second fluid from said second reservoir.

11. The method according to claim 10, further comprising:
    adjusting said supplementary dose of said second fluid from said second reservoir
    at least in part on said information about said content of said fluid element before ejection of said supplementary dose.

12. A medical device, comprising:
    a first reservoir containing a first fluid medicament and a second reservoir containing a second fluid,
    a fluid element connected to said first reservoir and said second reservoir and through which said first fluid medicament is to be ejected, and
    a control unit,
    wherein the control unit is configured to receive information about a desired dose of said first fluid medicament to be ejected,
    wherein the control unit is further configured to, in response to receiving the information about the desired dose of said first fluid medicament, receive information about a content of said fluid element,
    wherein the information about said content of said fluid element comprises at least one of an amount of first fluid medicament remaining in the fluid element after a previous ejection from said first reservoir and an amount of second fluid remaining in the fluid element after a previous ejection from said second reservoir,
    wherein the control unit is further configured to adjust said desired dose to an adjusted dose to be ejected from said first reservoir based at least in part on said information about the content of said fluid element, and
    wherein said first reservoir and said fluid element are configured to eject the adjusted dose.

13. The medical device according to claim 12, wherein said medical device is a portable medical device.

14. The medical device according to claim 13, wherein said portable medical device comprises a pen for injecting insulin or an infusion pump.

* * * * *